United States Patent [19]

Gough

[11] Patent Number: 4,671,288
[45] Date of Patent: Jun. 9, 1987

[54] ELECTROCHEMICAL CELL SENSOR FOR CONTINUOUS SHORT-TERM USE IN TISSUES AND BLOOD

[75] Inventor: David A. Gough, Cardiff by the Sea, Calif.

[73] Assignee: The Regents of the University of California, Berkeley, Calif.

[21] Appl. No.: 744,249

[22] Filed: Jun. 13, 1985

[51] Int. Cl.⁴ .............................................. A61B 5/00
[52] U.S. Cl. ................................... 128/635; 204/403; 204/415
[58] Field of Search ................. 128/635; 204/403, 415

[56] References Cited

U.S. PATENT DOCUMENTS 3,224,433 12/1965 Dalebor .............................. 128/635
4,197,852 4/1980 Schindler ............................ 128/635
4,366,033 12/1982 Richter et al. .................. 128/635 X
4,419,210 12/1983 Wang .............................. 128/635 X
4,545,382 10/1985 Higgins et al. ....................... 128/635

FOREIGN PATENT DOCUMENTS 0041190 4/1979 Japan .................................. 204/415
0169668 10/1982 Japan .................................. 128/635

Primary Examiner—Lee S. Cohen
Attorney, Agent, or Firm—Brown, Martin, Haller & Meador

[57] ABSTRACT

An electrochemical cell sensor for monitoring oxidizable enzyme substrates in biological fluids situated in a housing and suitable for implantation in the body, including at least one oxygen or hydrogen peroxide sensing electrode containing a suitable oxidase enzyme, a reference electrode, and a counter electrode all in communication with biological fluids through one or more openings in the walls of the housing.

24 Claims, 9 Drawing Figures

ELECTROCHEMICAL CELL SENSOR FOR CONTINUOUS SHORT-TERM USE IN TISSUES AND BLOOD

BACKGROUND OF THE INVENTION

A variety of biomedical sensors are routinely used by physicians or clinicians to monitor physiological variables such as respiratory rate, blood pressure, and temperature. A relatively new addition to the repertoire of biomedical sensors is the enzyme electrode. This is a sensor that combines certain analytical enzymatic techniques with commonly used chemical-selective electrodes. Enzyme electrodes enable the user to determine the concentration of certain biochemicals rapidly and with considerable accuracy. Currently there are enzyme electrodes that can detect urea, uric acid, glucose, various alcohols, and a number of amino acids when used in certain well-defined situations.

Of the available enzyme electrodes, perhaps the one that is most widely used is the glucose electrode, of which there exist several variations. The first report that enzymes could be used to measure glucose was that of Clark in U.S. Pat. No. 3,539,455. They proposed that glucose could be detected amperometrically using the enzyme glucose oxidase held between two membranes surrounding an oxygen or hydrogen peroxide electrode. As glucose and oxygen diffuse through the membrane, there was a reduction in oxygen concentration proportional to the concentration of glucose in the sample fluid as a result of the enzymatic process described below.

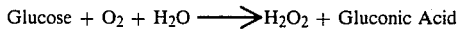

$$\text{Glucose} + O_2 + H_2O \xrightarrow{\text{Glucose oxidase}} H_2O_2 + \text{Gluconic Acid}$$

The electrode can be polarized cathodically to detect residual oxygen not consumed by the enzymatic proess or polarized anodically to detect the product of the enzyme reaction, hydrogen peroxide.

The glucose enzyme electrode was apparently first put into practice by Hicks et al. as described in U.S. Pat. No. 3,542,662. These inventors employed two oxygen electrodes, unlike the single electrode design of Clark, and immobilized glucose oxidase on one of them. A dual enzyme electrode configuration, where one electrode had immobilized enzyme, was intended to be insensitive to changes in oxygen levels not mediated through glucose oxidase. Glucose oxidase was immobilized by entrapment in a polyacrylamide gel matrix over one of the oxygen electrodes. Since this electrode was still sensitive to changes in oxygen tension, the difference between the output of the two oxygen electrodes was recorded to reflect glucose concentrations that were relatively independent of fluctuations in background oxygen concentration.

Additional changes in the overall design of the basic oxygen sensor as they relate to modifications in the enzyme membrane surrounding the sensor or to modifications in the electrodes are described in U.S. Pat. Nos. 4,356,074; 4,073,713; 1,442,303; 3,948,745; and 3,847,777, respectively. None of these modified enzyme oxygen sensing electrodes can be used to monitor in vivo levels of various enzyme substrates or their by-products.

It is desirable to have enzyme electrodes that can be implanted in patients to continuously monitor blood or tissue fluid concentrations. For instance, it is particularly desirable to have an implantable enzyme electrode sensor for use in diabetics, to continuously monitor glucose concentrations. While there exist a number of oxidase-based enzyme electrodes capable of detecting glucose or other substances such as alcohol and uric acid in vitro because of design features associated with these sensors, they are not suitable for use to detect these substances in vivo.

SUMMARY OF THE INVENTION

An enzyme electrode sensor is described for determining directly in the body the concentration of certain biochemicals, particularly glucose, alcohol or uric acid, comprising a fine needle that can be implanted subcutaneously in the blood stream or in other body compartments. The active region of the sensor is situated on the side of the needle rather than at the tip, thus permitting the construction of a small diameter needle sensor suitable for implantation and providing for sufficient sensitive area to produce an easily measured signal.

DETAILED DESCRIPTION OF THE INVENTION

It is the purpose of this invention to provide an electrochemical cell sensor for determining in situ the presence of certain biological molecules in bodily fluids where these molecules are substrates for or products produced by oxidase enzymes. Virtually any substrate that is capable of undergoing enzymatic oxidation with molecular oxygen and which involves an enzyme catalyst can be detected. For the purpose of description only, the invention will be elucidated as to its use in measuring glucose, but it will be understood to those skilled in the art that it is not so limited.

Figure 1:
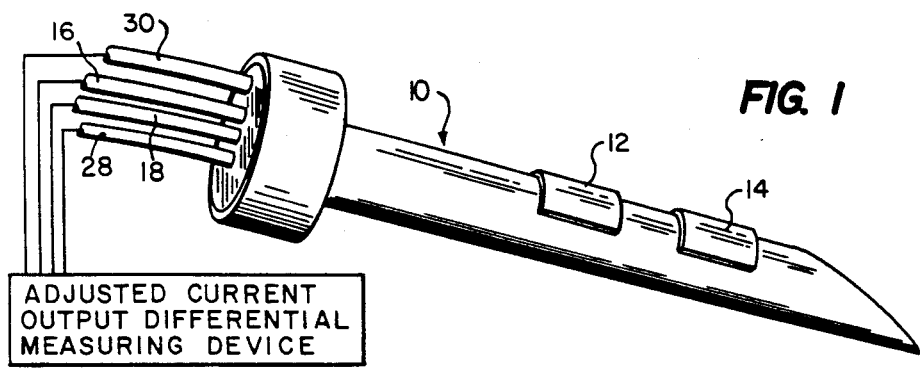
FIG. 1 is a perspective view of one configuration of the sensor.
Figure 2:
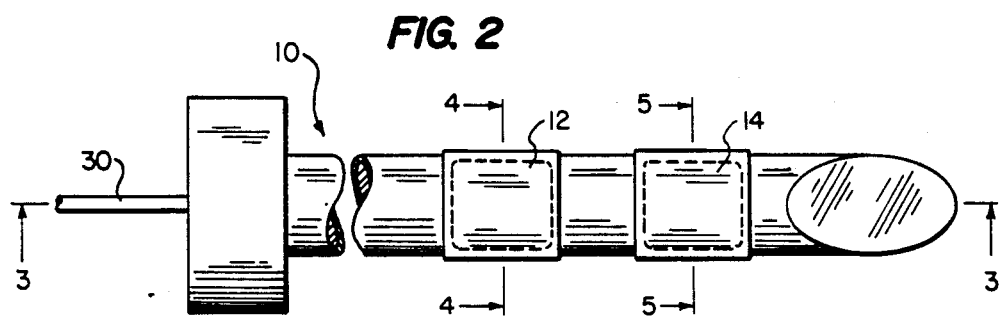
FIG. 2 is a top plan view of the sensor.
Figure 3:
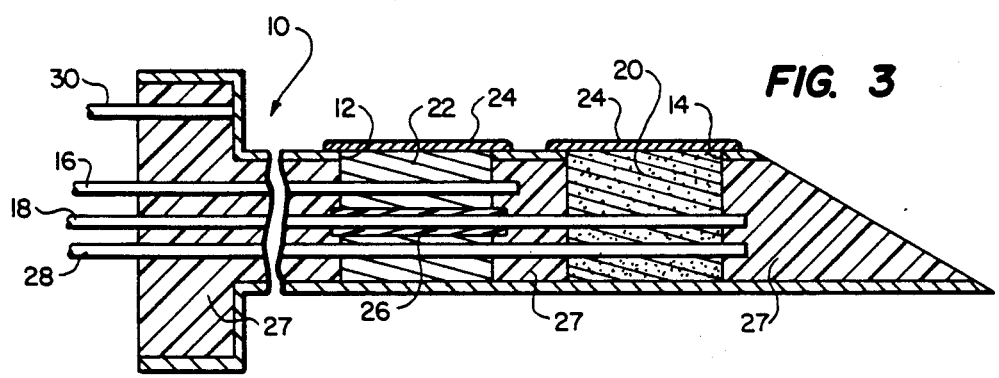
FIG. 3 is a sectional view taken on Line 3—3 of FIG. 2.

The electrochemical cell sensor shown in FIG. 1 comprises a housing 10 covered with biocompatible material, particularly useful is a fine hollow needle suitable for piercing the skin. In the preferred embodiment of the invention shown in FIG. 1, there are two elongated openings, 12 and 14, in the wall of the housing that provide a means whereby the interior of the housing can be in fluid communication with the external environment. FIG. 2 shows a top view of the openings 12 and 14. Situated in the housing shown in FIG. 3 at the respective openings are two oxygen sensors 16 and 18. An oxidase enzyme is situated physically near the surface of the sensor 18 by embedding it in a porous gel 20 that surrounds the sensor. This can be accomplished, for example, as described by G. Guilbault et al, in U.S. Pat. No. 3,948,745 by chemically binding an enzyme to a gel matrix, particularly useful are matrices composed of acrylamide or acrylic. The gel-forming material can be introduced into the space between the electrodes and the housing and crosslinked or polymerized in place. Alternatively, the sensor 18 can be covered by a porous membrane containing oxidase enzyme as described by Wingard et al. in *Journal of Biomedical Materials Research* (1979, 13: 921–935). The second oxygen sensor 16 is utilized to monitor the oxygen concentration of the environment and, hence, is devoid of enzyme.

Figures 4, 5:
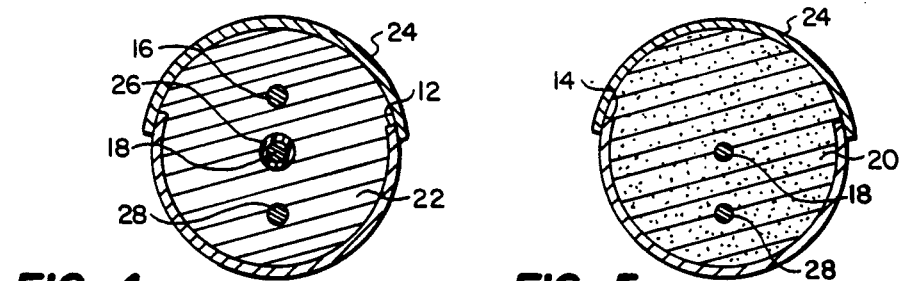
FIG. 4 is an enlarged sectional view taken on Line 4—4 of FIG. 3.
FIG. 5 is an enlarged sectional view taken on Line 5—5 of FIG. 3.

FIGS. 4 and 5 show cross-sectional views through the sensor at two different locations along the sensor. FIG. 4 shows both oxygen-sensing electrodes and the silver/silver chloride reference electrode, while FIG. 5 reveals only the oxygen sensing electrode embedded in an enzyme gel matrix and the reference electrode.

In the design in which the electrode that is in contact with the enzyme gel is polarized as an anode or detection of the enzymatic product, hydrogen peroxide, the second electrode is still polarized cathodically to determine oxygen concentration. In this case, glucose is determined directly from the signal of the anode, and the oxygen sensor is used for the determination of oxygen to assure that sufficient oxygen is present to not limit the enzyme reaction.

In those instances where the first sensor 18 is embedded in a gel matrix containing enzyme, the second oxygen sensor is similarly embedded in a matrix 22 but lacking enzyme. The openings in the housing beneath which the sensors are situated may be covered with a thin porous material 24 in those instances where the electrochemical cell sensor is implanted in oxygen poor tissue. To avoid low oxygen concentrations from being rate limiting in the enzymatic reaction, the material chosen should permit the electrochemical cell structure to remain sensitive to glucose over a useful range of concentrations in the presence of relatively low oxygen concentrations. This is accomplished by selecting a material that restricts the diffusion or partitioning of glucose while remaining relatively permeable to oxygen. Typically such membranes are made either of porous or perforated polydimethylsiloxane (Silastic). Alternatively, the diffusion of glucose can be controlled by incorporating domains of hydrophobic material in the gel on which the enzyme is embedded or attached, as suggested by D. Gough in U.S. Pat. No. 4,484,987.

Each chemical sensor is situated in the electrochemical cell structure housing at a different opening, and preferably near the center of the housing. The two sensors are insulated from each other with suitable insulating material 26 and 27, such as fused glass or epoxy. The sensor wires extend down the housing and emanate from its hub allowing for connection to instrumentation routinely utilized in electrochemical monitoring procedures.

Additionally contained in the electrochemical cell structure housing is a reference electrode 28 made of material well know to those in the art, a common example being chlorided silver. The reference electrode is preferably situated close to a unshielded segment of the two electrode sensors, and also extends out of the hub of the housing and is connected to the instrumentation. Lastly, the housing serves as a fourth electrode, a common counter electrode to which current of the two electrode sensors flow. The housing is similarly connected to instrumentation by attachment to a wire 30 at the hub.

When the electrochemical cell structure is implanted into biological tissues or fluids containing glucose and oxygen, these substances communicate with the respective sensors by ingress through the openings of the housing. Upon applying the characteristic potential between the respective sensors and the reference electrode, current passes between the sensors and the housing counter electrode, resulting in the immediate consumption of oxygen at the sensor surfaces. The sensor 18 that contacts the oxidase enzyme containing membrane experiences a reduction in oxygen flux or oxygen produced current compared to the second sensor 16 due to prior consumption of oxygen by the enzymatic process. This relative decrease in current is a function of the glucose concentration present. Thus, the amount of glucose is determined by the differential current output from the two sensors. The output can be quantified using operational amplifier circuitry.

In the design incorporating the hydrogen peroxide anode, the current from that sensor is proportional to glucose concentration, provided that sufficient oxygen is present in the tissue to not limit the enzyme reactions. This limit is determined by the second oxygen sensor. When the oxygen signal is lower than the glucose signal, the latter is disregarded.

Figure 6:
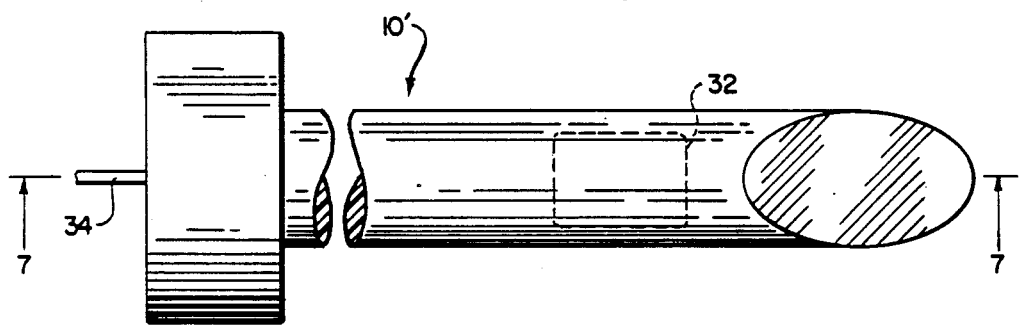
FIG. 6 is a top plan view of an alternative configuration of the sensor.
Figure 7:
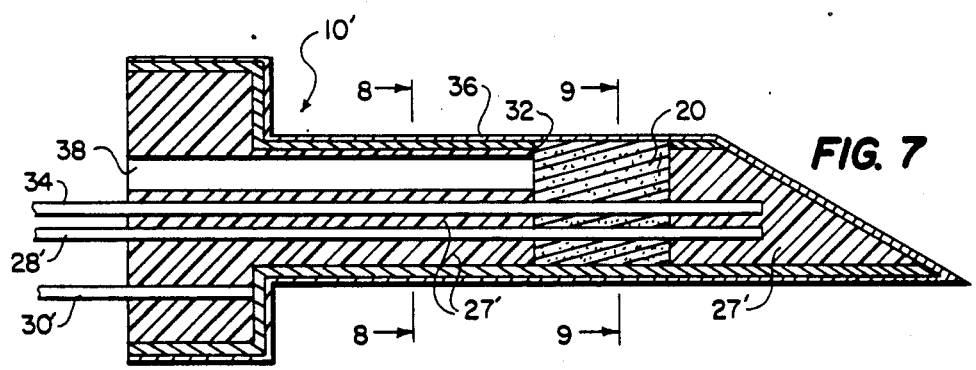
FIG. 7 is a sectional view taken on Line 7—7 of FIG. 6.

A second embodiment of the invention is shown in FIGS. 6 and 7. The electrochemical cell structure again comprises a housing 10' with an opening 32 in a side of the housing, and again a fine hollow needle capable of piercing the skin being preferred for use as the housing. FIG. 7 shows that within the housing is a single oxygen-sensing noble-metal electrode 34 embedded in a gel matrix 20' containing enzyme as described earlier. Alternatively, the electrode can be covered with an oxidase enzyme containing membrane. Additionally, the electrochemical cell sensor contains a silver/silver chloride reference electrode 28' and a counter electrode 30', the needle housing acting as the counter electrode. All three electrodes are connected to appropriate recording instrumentation by wire leads that contact the electrodes at the position where they emanate from the housing. The entire housing is covered with biocompatible material 36 that is permeable to small molecular weight substance, which permits the diffusion of oxygen in the bodily fluids into the interior of the housing.

In those instances when the electrochemical cell structure is implanted in regions of the body where there are low oxygen concentrations, it is desirable to fabricate the gel matrix or its outer layer of a material that permits the electrochemical cell sensor to remain sensitive to glucose over a useful range of concentrations in the presence of such low oxygen levels. This is accomplished by selecting a material that restricts the diffusion or partitioning of glucose while remaining relatively permeable to oxygen. As described above, the diffusion of glucose can be controlled by incorporating domains of hydrophobic material in a gel matrix in which the oxidase enzyme is embedded and which contacts the oxygen sensor. Alternatively, a membrane of Silastic or other such hydrophilic material can be positioned between the gel matrix and the external environment. The nonworking regions of the oxygen electrode and the silver/silver chloride electrode are insulated with suitable insulating material 26'. Particularly useful is epoxy or fused glass. The working regions of the electrodes are situated near the opening or openings in the electrochemical housing wall and are not insulated.

In order to assure the accessibility of oxidase enzyme associated with the oxygen sensing electrode to oxygen, the preferred position of the electrode is near the opening in the housing. Additionally, a tunnel 38 is desirable that connects the oxygen-sensing regions with the external environment to allow for ingress of oxygen from the outside. By providing atmospheric oxygen to the enzyme electrode sensing region, the oxidase enzyme reaction is limited mainly by glucose and not by oxygen. Consequently, it is possible to monitor glucose or other enzyme substrates without a oxygen reference electrode.

Figure 8:
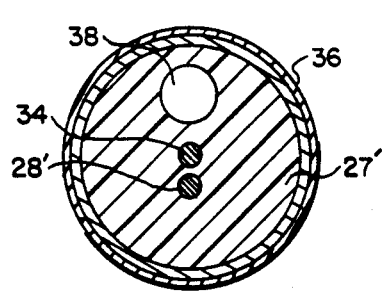
FIG. 8 is an enlarged sectional view taken on Line 8—8 of FIG. 7.
Figure 9:
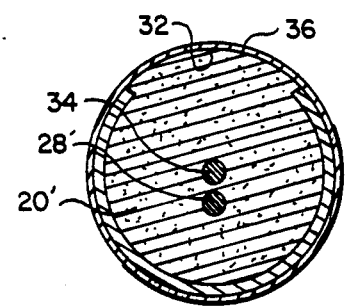
FIG. 9 is an enlarged sectional view taken on Line 9—9 of FIG. 7.

FIGS. 8 and 9 show cross-sectional views at different positions along the length of the sensor. FIG. 8 depicts the tunnel 38 and the oxygen sensing 34 and reference electrodes 28', while FIG. 9 shows the opening 32 and the oxygen sensing 34 and reference electrodes 28'.

It will be apparent to those skilled in the art that there are a variety of means available for supplying oxygen to the oxygen sensing region of the oxygen sensor. An alternative means is to charge a reservoir that communicates with the oxygen-sensing region with oxygen prior to implanting the electrode into the body. In this situation the oxygen would eventually be consumed, but the sensing lifetime would, nevertheless, be adequate for determining the concentrations of oxidase substrates.

The following example is described for illustrative purposes and should not be construed as narrowing the scope of the invention. It will be apparent to those skilled in the art that there exist many variations as to which particular steps of the invention may be practiced.

EXAMPLE

Determination of glucose in bodily fluids can be carried out by measuring the oxidation of glucose in the presence of oxygen by the enzyme glucose oxidase. It is possible using an enzyme electrode (shown in FIG. 1) to measure the concentration of glucose after implanting an electrochemical cell sensor containing two oxygen sensors, one of which is in communication with glucose oxidase. The latter is positioned over the sensor by embedding it in a crosslinked collagen matrix as described by D. A. Gough, J. K. Leypoldt, and J. C. Armour in *Diabetes Care* (1982, 5: 190–198). The electrochemical cell sensor containing the sensors situated in a housing were inserted subcutaneously near the surface in the leg region of an anesthetized dog. Glucose was infused intravenously through a venous catheter, and at various time intervals thereafter the resulting blood glucose concentration monitored by analyzing the differential signal coming from the sensors. Table 1 shows that after the sensors have stabilized, that there is a rapid and significant response by the sensors to the infused glucose.

In order to relate the levels of glucose present to the glucose dependent current changes, glucose levels were measured by standard laboratory methods using a blood glucose analyzer.

TABLE 1

Detection of Blood Glucose Levels with the Electrochemical Cell Sensor

| Time after glucose injection (minutes) | 0.5 | 1.0 | 3.0 | 20.0 | 30.0 | 40.0 | 50.0 | 60.0 |
|---|---|---|---|---|---|---|---|---|
| Blood glucose (mg/deciliter) | 450 | 200 | 140 | 115 | 100 | 80 | 75 | 70 |
| Glucose-dependent difference current (nano amps) | 0 | 0 | 0 | 5 | 15 | 20 | 25 | 30 |

I claim:

1. An electrochemical cell sensor capable of being implanted into an animal body comprising:
   a housing with an opening or openings in the wall of said housing;
   said housing comprising a hollow needle composed of platinum or stainless steel, and said housing and said opening or openings covered with a layer of porous biocompatible material;
   electrode means situated in said housing and in fluid communication via said opening or openings with fluids present in said animal body and responsive to enzyme substrates or products present in said fluid; and a means for relating said response of said electrode means to the concentration of said enzyme substrates or products present in said fluids.

2. An electrochemical cell sensor as defined in claim 1 wherein said electrode means is comprised of four (4) electrodes:
   an enzyme substrate or product dependent sensing electrode composed of a noble metal and in communication with an oxidase enzyme,
   an enzyme substrate independent oxygen-sensing electrode composed of a nobel metal,
   a reference electrode composed of silver/silver chloride, and
   a common counter electrode, said common counter electrode being said housing.

3. An electrochemical cell sensor as defined in claim 2 wherein said 4 electrodes are insulated.

4. An electrochemical cell sensor as defined in claim 3 wherein said oxidase enzyme is drawn from the group consisting of glucose oxidase, lactate oxidase, uricase, or alcohol oxidase.

5. An electrochemical cell sensor as defined in claim 4 wherein said enzyme substrates are drawn from the group consisting of glucose, lactate, uric acid, ethanol, or oxygen.

6. An electrochemical cell sensor as defined in claim 5 wherein said means of relating said response of said electrode means to the concentration of said enzyme substrates or products in said fluids is by an apparatus that measures the adjusted current output differential of said electrode means.

7. An electrochemical cell sensor as defined in claim 6 wherein said means for relating said response of said electrode means to the concentration of said enzyme substrates or products in said fluids is by an apparatus that measures the adjusted current of the substrate or product sensing electrode and indicates said concentration of said enzyme substrates or products when the concentration of oxygen is sufficiently high as indicated by said enzyme substrate independent oxygen sensing electrode.

8. An electrochemical cell sensor capable of being implanted in an animal body comprising an electrically conductive hollow needle housing with one or more openings in the walls of said electrically conductive hollow needle housing; an electrode means situated in said housing and in fluid communication via said opening or openings with fluids present in said animal body and responsive to enzyme substrates or products in said fluids, said electrode means comprising four (4) electrodes, an enzyme substrate or product dependent sensing electrode, composed of a noble metal and in communication with an oxidase enzyme, an enzyme substrate independent oxygen-sensing electrode composed of a noble metal, a reference electrode composed of silver/silver chloride and a common counter electrode being said hollow needle housing; and a means for differentially regulating the accessibility of said enzyme substrates or products to said electrode means, and a means for relating said response of said electrode means to the concentration of said said enzyme substrates or products present in said fluids.

9. An electrochemical cell sensor as defined in claim 8 wherein said 4 electrodes are insulated.

10. An electrochemical cell sensor as defined in claim 9 wherein said oxidase enzyme is drawn from the group consisting of glucose oxidase, lactate oxidase, uricase, and alcohol oxidase.

11. An electrochemical cell sensor as defined in claim 10 wherein said enzyme substrates are drawn from the group consisting of glucose, lactate, uric acid, ethanol, or oxygen.

12. An electrochemical cell sensor as defined in claim 11 wherein said means for differentially regulating the accessibility of said enzyme substrates or products comprises material with enzyme substrate selective diffusion properties situated over said opening or openings in said walls of said electrochemical cell sensor hollow needle housing.

13. An electrochemical cell sensor as defined in claim 12 wherein said material with enzyme substrate selective diffusion properties is less restrictive of the diffusion of oxygen than of other enzyme substrates.

14. An electrochemical cell sensor as defined in claim 13 wherein said means of relating said response of said electrode means to the concentration of said enzyme substrates or products is by an apparatus that measures the adjusted current output differential of said electrode means.

15. An electrochemical cell sensor as defined in claim 14 wherein said means of relating said response of said electrode means to the concentration of said enzyme substrates or products in said fluids is by an apparatus that measures the adjusted current of the product or substrate sensing electrode and indicates said concentration of said enzyme substrates or products when the concentration of oxygen is sufficiently high as indicated by said enzyme substrate independent oxygen sensing electrode.

16. An electrochemical cell sensor capable of being implanted into an animal body comprising:

a hollow needle housing with one opening in the walls of said housing, an electrode means situated in said housing and in fluid communication via said opening with fluids present in said animal body and responsive to enzyme substrates present in said fluids, a means for supplying oxygen to said electrode means, and a means for relating said response of said electrode means to the concentration of said enzyme substrates in said fluids.

17. An electrochemical cell sensor as defined in claim 16 wherein said hollow needle housing is composed of platinum or stainless steel and said housing and said opening are covered with a layer of porous biocompatible material.

18. An electrochemical cell sensor as defined in claim 17 wherein said electrode means comprises three (3) electrodes:

an enzyme substrate or product dependent sensing electrode composed of a noble metal and in communication with an oxidase enzyme, a reference electrode composed of silver/silver chloride, and a common counter electrode being said hollow needle housing.

19. An electrochemical cell sensor as defined in claim 18 wherein said the enzyme substrate or products dependent sensing electrode is polarized cathodically to determine oxygen.

20. An electrochemical cell sensor as defined in claim 18 wherein said enzyme substrate or product dependent sensing electrode is polarized anodically to determine hydrogen peroxide.

21. An electrochemical cell sensor as defined in claim 18 wherein said means for supplying oxygen is a tunnel that provides communication of atmospheric oxygen with said electrode means.

22. An electrochemical cell sensor as defined in claim 21 wherein said electrode means is insulated.

23. An electrochemical cell sensor as defined in claim 22 wherein said oxidase enzyme is drawn from the group consisting of glucose oxidase, lactate oxidase, uricase, or alcohol oxidase.

24. An electrochemical cell sensor as defined in claim 23 wherein said enzyme substrates are drawn from the group consisting of glucose, lactate, uricase, ethanol, or oxygen.

* * * * *